US011903397B2

(12) United States Patent
Sindou et al.

(10) Patent No.: US 11,903,397 B2
(45) Date of Patent: Feb. 20, 2024

(54) HAY PRESERVATIVE AND METHODS FOR PRESERVATION OF HAY

(71) Applicant: DANSTAR FERMENT AG, Zug (CH)

(72) Inventors: Julien Sindou, Blagnac (FR); Henri Durand, Blagnac (FR)

(73) Assignee: DANSTAR FERMENT AG, Zug (CH)

(*) Notice: Subject to any disclaimer, the term of this patent is extended or adjusted under 35 U.S.C. 154(b) by 0 days.

(21) Appl. No.: 15/528,998

(22) PCT Filed: Nov. 24, 2015

(86) PCT No.: PCT/IB2015/059079
§ 371 (c)(1),
(2) Date: May 23, 2017

(87) PCT Pub. No.: WO2016/083996
PCT Pub. Date: Jun. 2, 2016

(65) Prior Publication Data
US 2017/0311625 A1 Nov. 2, 2017

(30) Foreign Application Priority Data
Nov. 24, 2014 (FR) .................................. 14194567.5

(51) Int. Cl.
*A23K 10/14* (2016.01)
*A23K 30/00* (2016.01)
(Continued)

(52) U.S. Cl.
CPC ................ *A23K 10/14* (2016.05); *A01N 3/00* (2013.01); *A23K 30/00* (2016.05); *C12N 1/20* (2013.01);
(Continued)

(58) Field of Classification Search
CPC .......... A23K 10/14; A23K 30/00; C12N 1/20; C12N 9/2442; C12R 1/01; A01N 3/00; C12Y 302/01014
See application file for complete search history.

(56) References Cited

U.S. PATENT DOCUMENTS 4,820,531 A 4/1989 Tomes
5,371,011 A 12/1994 Bernier et al.
(Continued)

FOREIGN PATENT DOCUMENTS

CN 104146151 A 11/2014
EP 0408220 A2 1/1991
(Continued)

OTHER PUBLICATIONS

Zarei et al. "Characterization of a Chitinase with Antifungal Activity from a Native Serratia Marcescens B4A" Brazilian Journal of Microbiology (2011) 42: 1017-1029, (pp. 1017-1029) (Year: 2011).*
(Continued)

*Primary Examiner* — Blaine Lankford
*Assistant Examiner* — Lauren K Van Buren
(74) *Attorney, Agent, or Firm* — NIXON & VANDERHYE

(57) ABSTRACT

There is provided a method of treating hay for preventing and/or reducing heat damage in high moisture hay and as well to preserve the same, the method including adding to hay a hay preservative including a hay preserving and heat reducing effective amount of at least one enzyme having a chitinase activity, either alone or in combination with a hay preserving and heat reducing effective amount of a yeast of the genus *Pichia* or a bacteria of the genus *Pediococcus*. There is also provided a method of treating hay for preventing and/or reducing heat damage in high moisture hay and as well to preserve the same, the method including adding to (Continued)

hay a hay preservative including a hay preserving and heat reducing effective amount of yeast of the genus *Pichia*.

16 Claims, 4 Drawing Sheets

(51) Int. Cl.
    *C12N 1/20*     (2006.01)
    *C12N 9/42*     (2006.01)
    *A01N 3/00*     (2006.01)
    *C12R 1/01*     (2006.01)

(52) U.S. Cl.
    CPC ........... *C12N 1/205* (2021.05); *C12N 9/2442* (2013.01); *C12Y 302/01014* (2013.01); *C12R 2001/01* (2021.05)

(56) References Cited

U.S. PATENT DOCUMENTS

2002/0031504 A1    3/2002    Beudeker
2005/0050595 A1*   3/2005    Muller ............... C12N 15/8285
                                                                    536/23.6

FOREIGN PATENT DOCUMENTS

| JP | S48-056819 A | 8/1973 | |
|---|---|---|---|
| JP | H11-196860 A | 7/1999 | |
| JP | 2000-109405 A | 4/2000 | |
| WO | 92/10945 A1 | 7/1992 | |
| WO | WO-9945787 A1 * | 9/1999 | ............. A01N 63/04 |

OTHER PUBLICATIONS

Singh et al "Purification and Characterization of Chitinase from *Paenibacillus* sp. D1" Applied Biochemistry and Biotechnology 164, 77-88(2011). Published online Oct. 29, 2010 (Year: 2010).*

Wittenberg et al. "Nutritive value of high moisture alfalfa hay preserved with Pediococcus pentosaceus" Canadian Journal of Animal Sciences (Year: 1994).*

Borreani et al. "The Effect of a Baler Chopping System on Fermentation and Losses of Wrapped Big Bales of Alfalfa" Agronomy Journal (Jan. 2006) (Year: 2006).*

Babji et al. thesis "Post-Harvest Resistance to Fungal attack in Alfalfa" University of Manitoba, Jul. 1997 (Year: 1997).*

Patel et al. "Purification and Characterization of an Extracellular Dextransucrase from Pediococcus pentosaceus isolated from soil of North East India" Food Technology and Biotechnology (Jan. 2011) (Year: 2011).*

M.B. Brurberg, et al., Expression of a chitinase gene from Serratia marcescens in Lactococcus lactis and Lactobacillus plantarum, Applied Microbiology and Biotechnology, 1994, pp. 108-115, vol. 42, Springer-Verlag.

Matilda Olstorpe, et al., *Pichia anomala* yeast improves feed hygiene during storage of moist crimped barley grain under Swedish farm conditions, Animal Feed Science and Technology, 2010, pp. 47-56, vol. 156, Elsevier B.V.

Stina Petersson, et al., Biocontrol of Mold Growth in High-Moisture Wheat Stored under Airtight Conditions by Pichia anomala, Pichia guilliermondii, and *Saccharomyces cerevisiae*, Applied and Environmental Microbiology, Mar. 1995, pp. 1027-1032, vol. 61, No. 3.

H. Zahiroddini, et al., Effects of Microbial Inoculants on the Fermentation, Nutrient Retention, and Aerobic Stability of Barley Silage, Asian-Australasian Journal of Animal Sciences, Oct. 2006, pp. 1429-1436, vol. 19, No. 10.

Z.G. Weinberg, et al., New trends and opportunities in the development and use of inoculants for silage, FEMS Microbiology Reviews, 1996, pp. 53-68, vol. 19, Elsevier.

Mehmet Levent Ozduven, et al., The Effects of Bacterial Inoculants and/or Enzymes on the Fermentation, Aerobic Stability and in vitro Dry and Organic Matter Digestibility Characteristics of Triticale Silages, Kafkas Universitesi Veteriner Fakultesi Dergisi, 2010, pp. 751-756, vol. 16, No. 5.

Ulrika Druvefors, et al., Efficacy of the biocontrol yeast *Pichia anomala* during long-term storage of moist feed grain under different oxygen and carbon dioxide regimens, FEMS Yeast Research, 2002, pp. 389-394, vol. 2.

Stina Petersson, et al., Pichia anomala as a biocontrol agent during storage of high-moisture feed grain under airtight conditions, Postharvest Biology and Technology, 1999, pp. 175-184, vol. 15, Elsevier B.V.

R.P. Tengerdy, et al., Ensiling Alfalfa with Additives of Lactic Acid Bacteria and Enzymes, Journal of the Science of Food and Agriculture, 1991, pp. 215-228, vol. 55, No. 2.

Office Action issued in Colombian Patent Application No. NC2017/0005171 dated Mar. 5, 2019, with English machine translation provided.

Office Action issued in Japanese Patent Application No. 2017-546270 dated Nov. 19, 2019, with English translation provided.

De Ingeniis et al., "Pichia anomala DBVPG 3003 Secretes a Ubiquitin-Like Protein That Has Antimicrobial Activity," Applied and Environmental Microbiology, vol. 75, No. 4, Feb. 2009, pp. 1129-1134.

Dehghani et al., "Effect of enzyme addition to forage at ensiling on silage chemical composition and NDF degradation characteristics," Livestock Science 150 (2012) 51-58.

First Examination Report issued in New Zealand Patent Application No. 731618 dated Nov. 23, 2018.

Notification of the First Office Action issued in Chinese Patent Application No. 201580063520.X dated May 7, 2020 with English translation provided.

Office Action issued in Chinese Patent Application No. 201580063520.X dated May 7, 2020.

Office Action issued in Japanese Patent Application No. 2020-174369 dated Sep. 21, 2021.

Ferrari et al., "A fast, sensitive and easy colorimetric assay for chitinase and cellulase activity detection," Biotechnology for Biofuels 2014 7:37, 8 pages.

Schiavone M, et al., "A combined chemical and enzymatic method to determine quantitatively the polysaccharide components in the cell wall of yeasts," FEMS Yeast Res. Sep. 2014;14(6):933-947. doi: 10.1111/1567-1364.12182. Epub Jul. 28, 2014. PMID: 25041403.

* cited by examiner

HAY PRESERVATIVE AND METHODS FOR PRESERVATION OF HAY

FIELD OF THE INVENTION

The present description relates to a hay preservative. More specifically to hay preservative for preserving hay in stored high moisture hay and method of use of hay preservative for the preservation of hay in stored high moisture hay.

BACKGROUND OF THE INVENTION

Wilting hay to an optimum moisture level in the field before baling would be an optimal situation in order to reduce dry matter (DM) loss, mold growth, and plant cell respiration during baling and storage of the hay. However, this process results in considerable nutritional losses due to continued respiration of plants, leaf shattering from mechanical damage and leaching due to rain. Recognition of this fact, and also because of unpredictable weather conditions, has led many hay producers to bale hay at higher than optimum moisture content (20-30%) to minimize the risk of rain damage and mechanical leaf losses. This practice, however, results in losses due to the activities of yeast and moulds, and sometimes bacteria and the resulting heating and poor nutritive quality of the hay at the time of feeding.

One simple approach has been to spray the moist hay at the time of storage with an organic acid, such as, for example, propionic acid. Although organic acids are generally effective in preventing fungal proliferation in moist hay, the higher rates of application, increased field, handling costs as well as environmental concerns make most hay producers reluctant to use them.

Although research shows that bacterial-based inoculants could potentially replace organic acids in the preservation of hay baled above optimum moisture content (Baah et al., Asian-Aust. 3. Anim. Sci. 18:649-660, 2005.) results of other studies on silage and haylage have been inconsistent (Zahiroddini et al., Asian-Aust. 3. Anim. Sci. 19(10):1429-1436, 2006, Muck, Trans. ASAE 47:1011-1016, 2004). There is ample evidence to indicate that the apparent inconsistencies in responses to inoculants are due to interactions between microbial species in individual inoculants and the epiphytic microbial (bacteria, yeast and molds) populations on hay prior to inoculation.

It would be highly desirable to be provided with an improved hay preservative, particularly for preventing and reducing heat damage of hay in stored high moisture hay and as well to preserve the same.

SUMMARY OF THE DISCLOSURE

The present disclosure provides a method of preserving hay quality in stored high moisture hay. The method relies on the use of a hay preservative capable of preventing and/or reducing heat damage in stored high moisture hay. The hay preservative used prevents and/or reduces heat in high moisture hay equally or better than organic acids.

In an aspect, there is provided a method of treating hay for preventing and/or reducing heat damage in high moisture hay and as well to preserve the same, the method comprising adding to hay a hay preservative comprising a hay preserving and heat reducing effective amount of at least one enzyme having a chitinase activity, either alone or in combination with a hay preserving and heat reducing effective amount of a yeast of the genus *Pichia* or bacteria of the genus *Pediococcus*. In another aspect, there is provided a method of treating hay for preventing and/or reducing heat damage in high moisture hay and as well to preserve the same, the method comprising adding to hay a hay preservative comprising a hay preserving and heat reducing effective amount of at least one enzyme having a chitinase activity.

In a further aspect, there is provided a method of treating hay for preventing and/or reducing heat damage in high moisture hay and as well to preserve the same, the method comprising adding to hay a hay preservative comprising a hay preserving and heat reducing effective amount of at least one enzyme having a chitinase activity in combination with a hay preserving and heat reducing effective amount of a yeast of the genus *Pichia*.

In yet a further aspect, there is provided a method of treating hay for preventing and/or reducing heat damage in high moisture hay and as well to preserve the same, the method comprising adding to hay a hay preservative comprising a hay preserving and heat reducing effective amount of at least one enzyme having a chitinase activity in combination with a hay preserving and heat reducing effective amount of a bacteria of the genus *Pediococcus*.

In another aspect, there is provided a method of treating hay for preventing and/or reducing heat damage in high moisture hay and as well to preserve the same, the method comprising adding to hay a hay preservative comprising a hay preserving and heat reducing effective amount of a yeast of the genus *Pichia*.

In a further aspect, there is provided a hay preservative comprising a hay preserving and heat reducing effective amount of at least one enzyme having a chitinase activity.

In yet a further aspect there is provided a hay preservative comprising a hay preserving and heat reducing effective amount of at least one enzyme having a chitinase activity in combination with a hay preserving and heat reducing effective amount of a yeast of the genus *Pichia* or bacteria of the genus *Pediococcus*.

In a furthermore aspect, there is provided a hay preservative comprising a hay preserving and heat reducing effective amount of at least one enzyme having a chitinase activity in combination with a hay preserving and heat reducing effective amount of a yeast of the genus *Pichia*.

In an aspect, there is provided a hay preservative comprising a hay preserving and heat reducing effective amount of at least one enzyme having a chitinase activity in combination with a hay preserving and heat reducing effective amount of a bacteria of the genus *Pediococcus*.

In a further aspect, all the previously mentioned aspects may further comprise at least one enzyme having a pectin lyase activity, a glucanase activity or a mixture thereof.

In another aspect, there is provided a hay preservative comprising a hay preserving and heat reducing effective amount of a yeast of the genus *Pichia*.

In a furthermore aspect, the is provided a high moisture hay comprising a hay preserving and heat reducing effective amount of yeast of at least one enzyme having a chitinase activity, either alone or in combination with a hay preserving and heat reducing effective amount of a yeast of *Pichia* genus or bacteria of *Pediococcus* genus. The high moisture hay may further comprise at least one enzyme having a pectin lyase activity, a glucanase activity or a mixture thereof.

In another aspect, there is provided a high moisture hay comprising a hay preserving and heat reducing effective amount of a yeast of the genus *Pichia*.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION

One of the problems with high moisture hay is spoilage and decay caused by spontaneously generated heat. These heated bales are usually poorer in color, nutritional value and have higher visible mold. One approach has been to spray the moist hay at the time of storage with an organic acid, such as, for example, propionic acid. Although organic acids are generally effective in preventing fungal proliferation in moist hay, the higher rates of application, increased field, handling costs as well as environmental concerns make most hay producers reluctant to use them.

Although research shows that bacterial-based inoculants could potentially replace organic acids in the preservation of hay baled above optimum moisture content results of other studies on silage and haylage have been inconsistent. There is ample evidence to indicate that the apparent inconsistencies in responses to inoculants are due to interactions between microbial species in individual inoculants and the epiphytic microbial (bacteria, yeast and molds) populations on hay prior to inoculation.

In its broadest aspect, the present disclosure provides a method of preserving hay quality and preventing or reducing heat damage in stored high moisture hay, the method comprising treating fresh hay under aerobic conditions with a hay preservative.

Figure 4:
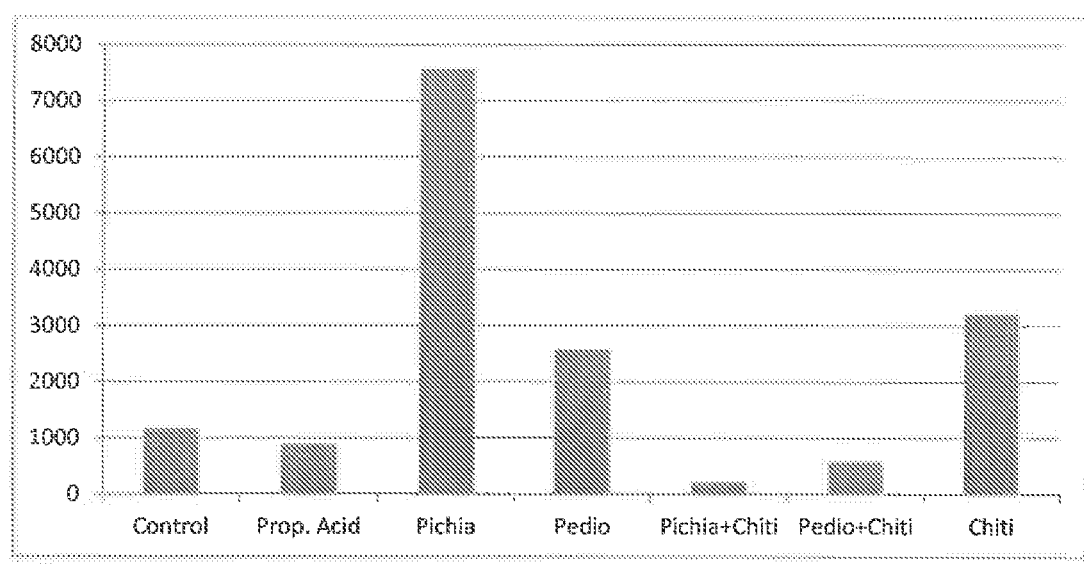
FIG. 4 illustrates a graph the time spent in minutes above 40° C. during storage (2013) of alfalfa hay bales treated with at least one enzyme having a chitinase activity in combination with a yeast of the genus *Pichia* (*Pichia*+Enz) or a bacteria of the genus *Pediociccus* (Pedio+Enz), compared to alfalfa hay bales treated with a yeast of the genus *Pichia* alone (*Pichia*), a bacteria of the genus *Pediociccus* alone (Pedio), Propionic acid (Prop. Acid) and non treated (Control).

The hay preservative comprises a hay preserving and heat reducing effective amount of at least one enzyme having a chitinase activity. Surprisingly, it has been found that the hay preservative is even further enhanced from the standpoint of its preservative effect and its capacity in preventing and/or reducing heat damage on high moisture hay if the at least one enzyme having a chitinase activity is combined with a yeast of the genus *Pichia* or bacteria of the genus *Pediococcus*. When the at least one enzyme having a chitinase activity is combined with a yeast of the genus *Pichia* or a bacteria of the genus *Pediococcus*, the temperature reduction of high moisture hay is significantly enhanced by the combination, in comparison with using each components of the combination alone as shown in FIG. 4.

Alternatively, the hay preservative may comprise a hay preserving and heat reducing effective amount of a yeast of the genus *Pichia* alone.

The term "hay preserving and heat reducing effective amount" when used herein will be understood to refer to an amount which is at least sufficient to preserve the quality of the hay. Thus the amount is at least sufficient to prevent and/or reduce heat damage in high moisture hay and as well to preserve the same.

The term "hay" when used herein will be understood to refer to all form of hay as the term is commonly used in agriculture. Hay is most commonly composed of alfalfa, grass, or mixtures of alfalfa and grass harvested at a target moisture level lower than 20%.

The method of treating hay for preventing and/or reducing heat damage in high moisture hay and as well to preserve the same may include adding to hay a hay preservative comprising a hay preserving and heat reducing effective amount of at least one enzyme having a chitinase activity. As mentioned previously, the at least one enzyme having a chitinase activity may be combined with a yeast of the genus *Pichia* or bacteria of the genus *Pediococcus*.

In an embodiment, the method of treating hay for preventing and/or reducing heat damage in high moisture hay and as well to preserve the same may include adding to hay a hay preservative comprising a hay preserving and heat reducing effective amount of at least one enzyme having a chitinase activity in combination with a hay preserving and heat reducing effective amount of a yeast of the genus *Pichia*.

In another embodiment, the method of treating hay for preventing and/or reducing heat damage in high moisture hay and as well to preserve the same may include adding to hay a hay preservative comprising a hay preserving and heat reducing effective amount of at least one enzyme having a chitinase activity in combination with a hay preserving and heat reducing effective amount of a bacteria of the genus *Pediococcus*.

Alternatively, the method of treating hay for preventing and/or reducing heat damage in high moisture hay and as well to preserve the same may include adding to hay a hay preservative comprising a hay preserving and heat reducing effective amount of a yeast of the genus *Pichia* alone.

The yeast of the genus *Pichia* includes, but is not limited to a *Pichia anomala* sp. In an embodiment, the yeast of the genus *Pichia* may be a *Pichia anomala* sp having all of the identifying characteristics of *Pichia anomala* having the accession number DBVPG 3003 strain. It is understood that any isolate having the identifying characteristics of *Pichia anomala* having the accession number DBVPG 3003 strain, including subcultures and variants thereof which have the identifying characteristics and activity as described herein are included. The *Pichia anomala* having the accession number DBVPG 3003 strain was deposited on Jan. 1, 1932 with the Industrial Yeast Collection DBVPG of the Dipartimento di Biologia Vegeta le e Biotecnologie Agroambientali e Zootecniche, Sezione di Microbiologia Agroalimentare ed Ambientale, http//www.agr.unipg.it/dbvpg, University of Perugia, Italy, by Castelli—Univ. Perugia, Italy and does not have restrictions on availability to the public.

The bacteria of the genus *Pediococcus* includes, but is not limited to a *Pediococcus pentosaceus* sp. In an embodiment, the bacteria of the genus *Pediococcus* may be from a *Pediococcus pentosaceus* sp having all of the identifying characteristics of *Pediococcus pentosaceus* BTC328 strain (having the accession number NCIMB 12674). In a further embodiment, the bacteria of the genus *Pediococcus* may be from a *Pediococcus pentosaceus* sp having all of the identifying characteristics of *Pediococcus pentosaceus* BTC401 strain (having the accession number NCIMB 12675). It is understood that any isolate having the identifying characteristics of the *Pediococcus pentosaceus* BTC328 or BTC401 strain, including subcultures and variants thereof which have the identifying characteristics and activity as described herein are included. The *Pediococcus pentosaceus* strains having the accession number NCIMB 12674 and 12675, which correspond to strains BTC328 and BTC401 respectively as noted above, were deposited on Feb. 17, 1988 with the National Collection of Industrial, Food and-Marine Bacteria Ltd, Ferguson Building, Craibstone Estate, Bucksburn, Aberdeen AB2I 9YA under the Budapest Treaty on the International Recognition of the Deposit of Microorganisms for the purpose of Patent Procedure by Biotal Limited, which is the predecessor in interest to Lallemand Animal. Nutrition UK Limited, which confirms that all restrictions on the availability to the public of the material so deposited will be irrevocably removed upon the granting of patent.

In one embodiment of the method, the treatment range for hay is typically $10^5$ to $10^{15}$ viable organisms of the yeast or bacteria per ton of hay, preferably $10^7$ to $10^{13}$ viable organisms of the yeast or the bacteria per ton of hay, and more preferably $10^9$ to $10^{12}$ viable organisms of the yeast or the bacteria per ton of hay. The term "ton" when used herein will be understood to refer to a metric ton (1000 kg).

The at least one enzyme having a chitinase activity may have a chitinase activity in a range of about 6 to about 300 enzyme units (U) per ton of hay to be treated. In an embodiment, the chitinase activity may be in range of about 6 to about 100 U per ton of hay to be treated. One U is defined as the amount of the enzyme that produces a certain amount of chitinase activity. Each enzyme unit (U) can liberate about 1.0 mg of N-acetyl-D-glucosamine from chitin (g) per hour at pH 6.0 and at a temperature of 25° C. in a 2 hour assay.

The hay preservative according to the present description may further comprise at least one enzyme having a Pectin lyase activity, a Glucanase activity or a mixture thereof.

The hay preservative according to the present description may be in either liquid of solid form. The hay preservative according to the present description may comprise a suitable carrier or may be used as is. In solid form, the hay preservative may comprise solid carriers or physical extenders. The suitable carrier may be in aqueous or non-aqueous liquid form or in solid form. Non limiting examples of aqueous or non-aqueous liquid form carrier include water, oils and paraffin. Non limiting examples of solid form carrier include organic or inorganic carrier such as, for example, malto-dextrin, starches, calcium carbonate, cellulose, whey, ground corn cobs, and silicone dioxide. The solid form can be applied directly to the hay in the form of a light powder dusting, or if it is disbursed in a liquid carrier it can successfully be sprayed on the hay. It is understood that any other suitable carrier for the purpose of the present description may be used. It is also understood that the hay preservative in accordance with the present disclosure may be applied to the hay using standard techniques common to those of ordinary skill in the art. The hay preservative may also be applied before, during and/or after bailing. The present invention will be more readily understood by referring to the following examples which are given to illustrate the invention rather than to limit its scope.

EXAMPLES

Example 1

Hay, Treatments and Baling Conditions

The hay was a third-cut consisting of 90% alfalfa and 10% brome grass. The hay was cut with a New-Holland™ disc-bine on Sep. 17, 2011 and left to dry unconditioned and undisturbed. Moisture level was evaluated using a Farmex™ windrow hay moisture tester (1205 Danner Drive, Aurora, Ohio) five days after cutting and found to be ranging from 20 to 35%. At this time the hay preservatives were prepared by pre-weighing inoculants and mixing each of them into separate jugs containing 6.5 L of pre-measured distilled water and shaken for 1 minute. A sprayer tank and spray boom with a single nozzle was mounted onto a 4790 Hesston big square baler. The boom was placed such that the spray pattern covered 90% of the windrow with minimal drifting.

Two trial bales were made to determine time to complete application of the additive on one bale, weight of the bale as well as a more accurate measure of moisture content of the baled material. Bale moisture was determined using a hay probe. Average time to make one bale (0.91 m×1.22 m×2.44 m) was found to be 2 minutes 30 seconds and average weight of bale was found to be 820 kg. The application rate of *P. anomala* was $10^{11}$ CFU in 1 L per ton of hay. The enzyme having a chitinase activity was applied at a rate of 1.5 g (suspended in 1 L of water) per ton of hay, corresponding to about 6 U per ton of hay. Propionic acid product consisted of 68% (vol/vol) propionic acid, and was applied at a rate of 2.72 L/ton and considered as a positive control. The negative control was water, and was applied at a rate of 1 L per ton of hay. The *P. anomala* and enzyme having a chitinase activity were obtained from Lallemand Specialties Inc. (Milwaukee, WI, USA) while the propionic acid was from Wausau Chemical Corporation (Wausau, WI, USA). Five replicate bales were made for each treatment. Samples of the *P. anomala* were taken after each application to verify the viability and numbers of the organism. This was to enable confirmation of the application rate for the organism. Each bale was labeled immediately following its exit from the baler using spray paint and later with tags attached to zip ties. All bales were weighed a day after baling and core sampled. Bales were left in the field for 2 weeks after baling, to reduce risk from combustion, before being transported and stored single-layered in an open sided hay-shed. Bales were cored sampled again on day 90 from 4 sides (excluding the top and bottom parts of the bales) and restacked on top or the others (piles of two bales). Core samples were taken again on day 180.

Chemical Microbiological Determination

Chemical and microbiological analyses were conducted on hay samples collected from six different sections of the field and on composite core samples obtained from four different locations on each bale on day 1, 90, and 180 of storage. Procedures outlined by McAllister et al. (1995. Intake, digestibility and aerobic stability of barley silage inoculated with mixtures of *Lactobacillus plantarum* and *Enterococcus faecium*. Can. J. Anim. Sci. 75:425-432.) were used for enumerating total bacteria, lactic acid producing bacteria (LAB), yeasts and molds. Dry matter (DM), organic matter (OM) and crude protein (CP) were determined according to AOAC (1990) procedures, and neutral detergent fibre (NDF), acid detergent fibre (ADF), and acid detergent insoluble nitrogen (ADIN) as described by Van Soest et al., (1991. Methods for dietary fiber, neutral detergent and non-starch polysaccharides in relation to animal nutrition. J. Dairy Sci. 74: 3583-3597.).

TABLE 1

Chemical composition (% DM), pH and microbiological composition (cfu $log_{10}$) of hay 90 days after treatment with various hay preservatives at baling.[1]

| Factor[2] | Day 0 | PA | CE | BPA | CON |
|---|---|---|---|---|---|
| DM | 81.95 | 87.32 | 86.59 | 86.08 | 84.68 |
| pH | 6.25 | 6.11 | 6.24 | 6.00 | 6.36 |
| TB | — | 7.14 | 6.60 | 6.10 | 7.51 |
| LAB | 3.80 | 5.42[bc] | 4.77[c] | 4.88[c] | 6.29[a] |
| YEAST | 6.48 | 5.57 | 5.94 | 5.38 | 6.20 |
| MOLD | 5.41 | 5.25 | 5.18 | 4.77 | 5.34 |
| OM | 87.89 | 88.10[a] | 85.28[c] | 88.27[a] | 88.02[a] |
| NH$_3$, mg kg$^{-1}$ | 0.336 | 0.479 | 0.841 | 0.583 | 1.017 |
| TN | 3.5 | 3.46 | 3.67 | 3.58 | 3.55 |
| LA, (g kg$^{-1}$) | — | 0.051[b] | 0.094[a] | 0.099[a] | 0.129[a] |
| NDF | 45.52 | — | — | — | — |
| ADF | 33.19 | 31.23 | 30.79 | 30.49 | 31.86 |
| ADIN | 0.375 | 0.273[ab] | 0.229[b] | 0.254[b] | 0.255[b] |
| ADIN, (% TN) | 10.75 | 7.92[ab] | 6.23[c] | 7.16[bc] | 7.19[bc] |

[1]PA = *Pichia anomala*; CE = Enzymes with Chitinase activity; BPA = Propionic Acid; CON = Control.
[2]TB = Non-fastidious bacteria growing on nutrient agar; LAB = bacteria growing on MRS presumed to be *Lactobacilli*; OM = Organic matter; NH$_3$ = Ammonia nitrogen; TN = Total nitrogen; LA = Lactic acid; ADF = Acid detergent fibre; ADIN = Acid detergent insoluble nitrogen Table 1 shows the effect of the hay preservatives treatments on chemical and microbiological profiles of samples of the hay collected on day 0 (day of baling) and 90 days post baling. Apart from lactic acid and acid detergent insoluble nitrogen (ADIN), the various treatments did not affect any of the factors evaluated, i.e., pH, total nitrogen, ammonia nitrogen and ADF. Lactic acid concentration was lower in *P. anomala* treatments compared to other treatments. Compared to other treatments the level of ADIN (% DM) was higher in the *P. anomala* treatment. The populations of total bacteria (non-fastidious bacteria growing on nutrient agar), yeast and mold in day 90 hay samples were not affected by treatment. Compared to other treatments, the populations of lactobacilli was higher in *P. anomala* and control bales having increased from $log_{10}$ 3.80 CFU g$^{-1}$ on the day of baling to $log_{10}$ 5.42 and $log_{10}$ 6.29 CFU g$^{-1}$, respectively on day 90.

TABLE 2

Chemical composition (% DM), pH and microbiological composition (cfu $log_{10}$) of hay 180 day post treatment with various inoculants at baling.[1]

| Factor[2] | PA | CE | BPA | CON |
|---|---|---|---|---|
| DM | 87.89[a] | 87.72[ab] | 85.64[b] | 85.79[b] |
| pH | 6.00[b] | 6.14[a] | 6.11[a] | 6.17[a] |
| NA | 6.14 | 7.25 | 7.23 | 7.23 |
| MRS | 5.21 | 6.32 | 6.28 | 6.74 |
| YEAST | 5.25[ab] | 5.82[a] | 4.67[b] | 4.27[b] |
| MOLD | 5.48 | 5.37 | 6.24 | 6.08 |
| OM | 88.59 | 87.93 | 87.80 | 87.63 |
| NH3 (mg•kg$^{-1}$) | 0.418 | 0.565 | 0.635 | 0.704 |
| TN | 3.26 | 3.57 | 3.56 | 3.53 |
| LA (g•kg$^{-1}$) | 0.983 | 0.970 | 1.052 | 1.453 |
| NDF | 44.18[b] | 44.78[b] | 46.33[b] | 50.07[a] |
| ADF | 32.35[bc] | 32.76[b] | 32.72[b] | 34.55[a] |
| ADIN | 0.262 | 0.253 | 0.245 | 0.268 |
| ADIN (% TN) | 8.03 | 7.17 | 6.96 | 7.58 |

[1]PA = *Pichia anomala*; CE = Enzymes with a chitinase activity; BPA = Propionic Acid; CON = Control.
[2]TB = Non-fastidious bacteria growing on nutrient agar; LAB = bacteria growing on MRS presumed to be *Lactobacilli*; OM = Organic matter; NH$_3$ = Ammonia nitrogen; TN = Total nitrogen; LA = Lactic acid; ADF = Acid detergent fibre; ADIN = Acid detergent insoluble nitrogen Apart from pH and the population of yeast, there were no differences between the treatments in chemical and microbiological composition in the day 180 samples (see Table 2). Compared to all other treatments, the pH was lowest in the *P. anomala* (6.00). The population of yeast was highest in the enzymes with a chitinase activity treatment.

TABLE 3

Volatile fatty acid (VFA) concentrations in hay core samples after 90 and 180 days post-treatment with various additives at baling[1]

| VFA | PA | CE | BPA | CON |
|---|---|---|---|---|
| Acetate (g kg$^{-1}$) | | | | |
| 90 d | 8.95 | 8.55 | 10.53 | 6.97 |
| 180 d | 9.69 | 9.58 | 8.38 | 7.28 |
| Propionate (g kg$^{-1}$) | | | | |
| 90 d | 0.1333 | 0.1267 | 0.4667[a] | 0.1467 |
| 180 d | 0.0675 | 0.080 | 0.426[a] | 0.052 |
| Total VFA (g kg$^{-1}$) | | | | |
| 90 d | 9.14 | 8.72 | 11.04 | 7.17 |
| 180 d | 9.87 | 9.76 | 8.89 | 7.42 |

[1]PA = *Pichia anomala*; CE = Enzyme with a chitinase activity; BPA = Propionic Acid; CON = Control.

Referring now to Table 3, total VFA (volatile fatty acid) and acetate concentrations in both the day 90 and day 180 samples were not affected by treatment. The predominant VFA produced after 180 days of storage was acetate and this accounted for 94% to 98% of the total VFA produced in the bales. There was a trend towards higher acetate and total VFA in bales treated with *P. anomala* and enzymes with a chitinase activity after 180 days of storage. Concentrations of acetate and total VFA in *P. anomala* and enzymes with a chitinase activity treated day 180 bales were at least 14% higher than the concentrations in the other treatments indicating that both of this treatment induced a greater degree of anaerobic microbial fermentation in the bales compared to the other treatments. Compared to the control treatment, total VFA and acetate concentrations were approximately 32% higher in *P. anomala*-enzymes with a chitinase activity treated day 180 bales. As expected, the propionate concentration in the propionic acid treated bales was higher than the concentrations in the other treatments in the d 90 and d 180 samples, respectively (Table 3).

TABLE 4

Quality Evaluation of hay treated with various additives and stored for 180 days.

| Quality Factor | Bale # | PA | CE | BPA | CON |
|---|---|---|---|---|---|
| COLOR | 1 | 5 | 18 | 10 | 17 |
|  | 2 | 17 | 18 | 5 | 5 |
|  | 3 | 17 | 10 | 12 | 5 |
|  | 4 | 5 | — | 10 | 10 |
|  | 5 | 17 | 0 | 7 | 15 |
|  | Mean | 12.2 | 15.3 | 8.8 | 10.4 |
| ODOR | 1 | 2 | 12 | 12 | 12 |
|  | 2 | 10 | 15 | 0 | 0 |
|  | 3 | 17 | 5 | 12 | 0 |
|  | 4 | 10 | 0 | 5 | 0 |
|  | 5 | 17 | 0 | 5 | 12 |
|  | Mean | 11.2 | 10.7 | 6.8 | 4.8 |
| OVERALL | 1 | 7 | 30 | 22 | 29 |
|  | 2 | 27 | 33 | 5 | 5 |
|  | 3 | 34 | 15 | 24 | 5 |
|  | 4 | 15 | 0 | 15 | 10 |
|  | 5 | 34 | 0 | 12 | 27 |
|  | Mean | 23.4 | 26 | 15.6 | 15.2 |
| GRADE | 1 | P | G | P | A |
|  | 2 | VG | G | VP | VP |
|  | 3 | G | P | P | VP |
|  | 4 | G | — | VP | VP |
|  | 5 | G | — | P | P |

PA = *Pichia anomala*; CE = enzymes with a chitinase activity; BPA = Propionic Acid; CON = Control.
Color/Odor—based on Maryland Cooperative Extension Fact Sheet # 644 'Evaluating Hay Quality' (http://www.extension.umd.edu/publications/pdfs/fs644.pdf).
Color
Hay with bright green color scores high (15 to 20).
Golden yellow to yellow hays score 5 to 15 points
Dark brown to black hays score 0 to 5 points.
Odor
Smell of new mown hay scores high (15 to 20 points).
Hays with musty or other off-odors score 5 to 15 points.
Moldy or unusually dusty hays score very low (0 to 5 points)
Grade
Grade is based on overall evaluation by examiner which included; very poor, poor, average, good, very good, and excellent All bales were opened on day 180 and their quality assessed based on the Maryland Cooperative Extension Fact Sheet #644. Based on the visual and sensory assessment, the control and propionic acid treatments produced hay of the poorest quality while the rest of the treatments produced hay of average to good quality (Table 4).

Temperature Stability

Temperature stability of the bales was monitored by continuously measuring the interior temperature of each bale with three Dallas Thermochron iButtons (Embedded Data Systems, Lawrenceburg, KY) that were inserted in the core holes the following morning after baling. The iButtons were configured to record temperatures every hour during the first 60 days of the storage period. Because temperature readings showed no further heating the probes were not placed back in the bales after 60 days. Bales were opened and visually scored for extent of spoilage and mold at the end of the storage period (180 d) based on the Maryland Cooperative Extension Fact Sheet #644 'Evaluating Hay Quality' (http://www.extension.umd.edu/publications/pdfs/fs644. pdf).

Figure 1:
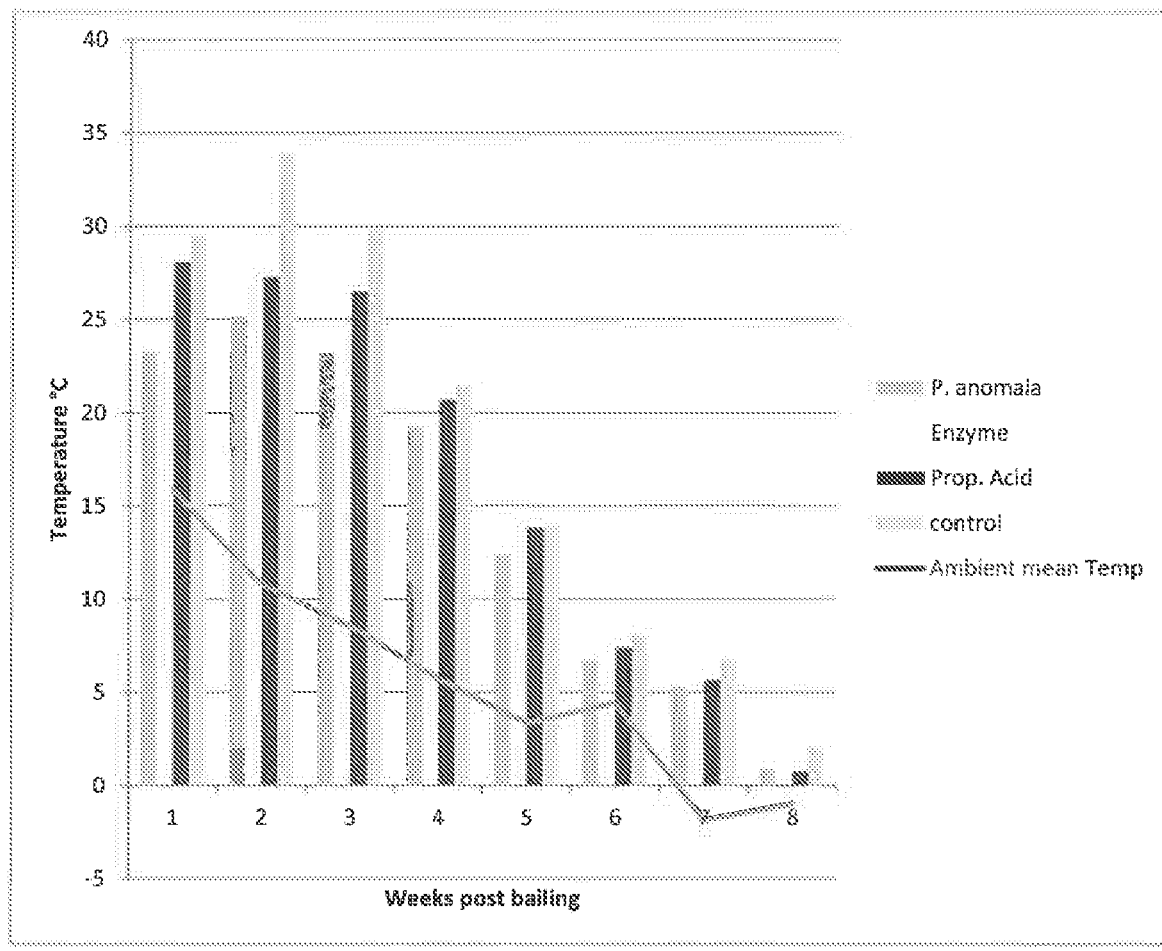
FIG. 1 illustrates the weekly mean temperature during storage of alfalfa hay bales treated with a yeast of the genus *Pichia* (*P. anomala*) or at least one enzyme having a chitinase activity (Enzyme); compared to alfalfa hay bales treated with Propionic acid (Prop. Acid) and non treated.
Figure 2:
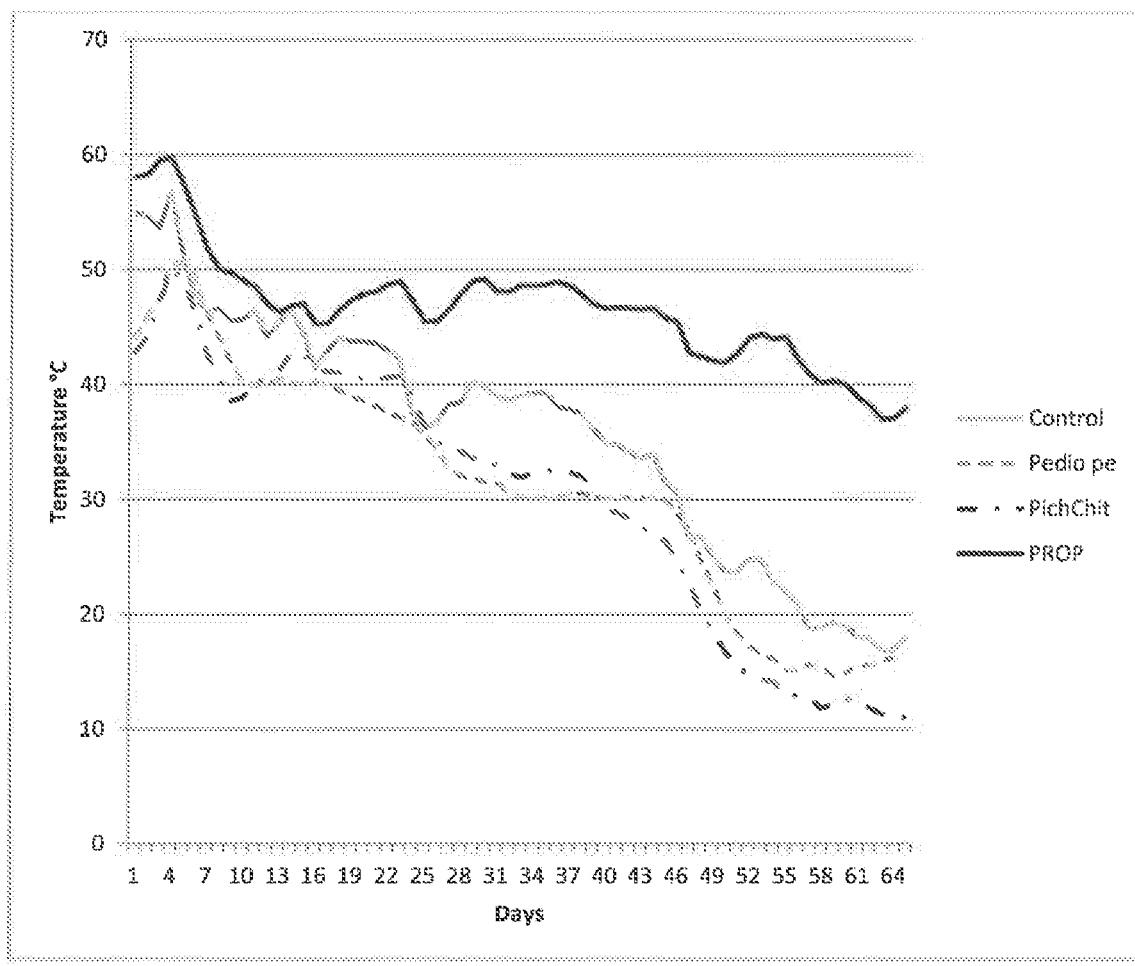
FIG. 2 illustrates the daily mean temperature during storage of alfalfa hay bales treated with at least one enzyme having a chitinase activity in combination with a hay preserving and heat reducing effective amount of a yeast of the genus *Pichia* (PichChit) or bacteria of the genus *Pediococcus* (Pedio pe), compared to alfalfa hay bales treated Propionic acid (PROP) and non treated.

As shown on FIG. 1, average weekly ambient (bale storage area) temperature reduced from a high of approximately 16° C. during the first week of storage to sub-zero temperatures after week 7. However, the temperatures in all bales remained above 20° C. during the first three weeks of the storage period. The highest weekly temperature (about 34° C.) was recorded during week 2 in control bales. The average temperature in control bales during the first three weeks was approximately 30° C. Temperatures in bales treated with enzymes with a chitinase activity were consistently lower than those in control bales from week 1 to week 7 (FIG. 1). A similar trend (except during week 2) was observed when the treatment was compared to the propionic acid treatment (FIG. 2). Although all the treatments had a positive effect on lowering temperature in bales during the storage period, the most effective treatment; compared to both the control and propionic acid treatments, were enzymes with a chitinase activity. Compared to the control and propionic acid treated bales, average temperatures in enzymes with a chitinase activity treated bales were 6-8° C. and 4-5° C. lower than temperatures in the control and propionic acid treated bales, respectively, during the same period.

Animal Experiment

In situ rate and extent of DM and NDF disappearance of the day 180 hay samples were determined in three cows fitted with ruminal cannulas and fed a standard feedlot backgrounding diet consisting of 50% timothy hay plus 50% barley silage (DM basis). Subsamples of the day 180 core samples obtained from bales treated with the same preservative were composited and ground to pass through a 4 mm screen. Approximately 4 g of each composite sample was weighed into Dacron bags and incubated in triplicate in each cow for 0, 2, 6, 12, 24, 48, 72, 96, and 120 h. Bags were made of monofilament polyester mesh (53 µm pore size, 5 cm×20 cm, Ankom, Fairport, New York). Cows were given two weeks to adapt to their diets before starting incubations. Immediately after incubation, bags were rinsed under cold tap water until all the rumen contents on the outside of the bags had been removed. Bags were washed in a domestic washing machine in cold water for three minutes using the delicate washing cycle without detergent and spin cycle. The washing procedure was repeated once. Duplicate sets of un-incubated bags containing samples of each treatment were washed with the bags above and used to estimate 0 h disappearance for each treatment. All bags were then dried in a forced-air oven at 55° C. for 48 h. The residues from triplicate bags of the same treatment incubated in the same cow were pooled and ground to pass through a 1 mm screen before being analyzed for NDF as per the method stated above. Percentage disappearance of DM and NDF were calculated from the proportion remaining in the bags after each incubation time. The DM and NDF disappearance data were fitted to a modified version of the exponential model of Orskov and McDonald (1979) with a lag phase:

$$p = a + b(1 - e^{-c(t-lag)}) \text{ for } t > lag$$

where; p is DM or NDF disappearance (%) after t hours, a is the fraction which disappears rapidly (%), b is the slowly disappearing fraction (%), and c is the fractional rate of disappearance ($h^{-1}$) of fraction b. The parameters were estimated by an iterative nonlinear procedure (Marquardt method) with the SAS (1990) software package. Effective disappearance (EFFD, %) at 48 h of incubation was estimated based on an assumed fractional outflow rate of 6%.

TABLE 5

Effect of hay preservative[1] on in situ DM disappearance (%)[2] of alfalfa-brome hay incubated in the rumen of Jersey cows

| Disappearance[3] | PA | CE | BPA | CON |
|---|---|---|---|---|
| 12 h | 66.65[a] | 62.92[c] | 62.20[c] | 61.38[c] |
| 24 h | 75.13[a] | 72.65[b] | 72.84[b] | 70.86[c] |
| 48 h | 78.37[a] | 77.22[a] | 78.57[a] | 75.62[b] |

TABLE 5-continued

Effect of hay preservative[1] on in situ DM disappearance (%)[2]
of alfalfa-brome hay incubated in the rumen of Jersey cows

| Disappearance[3] | PA | CE | BPA | CON |
|---|---|---|---|---|
| Kinetics | | | | |
| a | 34.13 | 34.65 | 33.34 | 34.37 |
| b | 44.62$^{ab}$ | 43.21$^{b}$ | 46.38$^{a}$ | 42.11$^{b}$ |
| c, h$^{-1}$ | 0.114$^{a}$ | 0.089$^{bc}$ | 0.083$^{c}$ | 0.087$^{c}$ |
| Potential | 78.75$^{a}$ | 77.86$^{ab}$ | 79.72$^{a}$ | 76.48$^{b}$ |
| Effective | 62.92$^{a}$ | 60.40$^{b}$ | 59.97$^{b}$ | 59.09$^{b}$ |

[1] PA = *Pichia anomala*; CE = enzymes with a chitinase activity BPA = Propionic Acid; CON = Control.
[2] Means in the same row with different superscripts differ (P < 0.05).
[3] Parameters calculated from the fitted equation: $p = a + b[1 - e^{-c(t-lag)}]$ for $t >$ lag; where p is the proportion (%) of NDF disappearing from nylon bags after t hours of incubation; a is the rapidly disappearing fraction (%); b is the slowly disappearing fraction (%); c is the fractional rate of disappearance (h$^{-1}$) of fraction b In Sacco Dry Matter Disappearance The effects of the preservatives on 12, 24, and 48 h DM disappearance, including kinetics of disappearance are illustrated in Table 5. There was no lag time in DM disappearance. Hay samples treated with the microbial additive (*P. anomala*) had higher DM disappearance at all incubation time points (12, 24 and 48 h) compared the control and propionic acid treatments; except at 48 h when all the additives (including enzymes with a chitinase activity and propionic acid) were higher than the control. Similarly, both the rate and effective DM disappearance were higher in hay samples treated with the microbial additives compared to the control and propionic acid treatments. Compared to all other treatments, hay samples from bales treated with *P. anomala* had the fastest rate of DM disappearance (0.114 h$^{-1}$. The lowest rate of 0.083 h$^{-1}$ and 0.087 h$^{-1}$ were observed in the propionic acid treatment and control treatments. All the additives increased the potentially digestible DM fraction, except enzymes with a chitinase activity which had a similar value to that of the control. That notwithstanding, effective DM disappearance in the sample treated with *P. anomala* was higher than in the control and propionic acid treatments.

TABLE 6

Effect of hay preservatives[1] on in situ NDF disappearance (%)[2] of alfalfa-brome hay incubated in the rumen of Jersey cows

| Disappearance[3] | PA | CE | BPA | CON |
|---|---|---|---|---|
| 12 h | 41.06$^{b}$ | 37.28$^{c}$ | 39.04$^{bc}$ | 39.64$^{bc}$ |
| 24 h | 51.88$^{ab}$ | 49.22$^{b}$ | 51.88$^{ab}$ | 51.11$^{b}$ |
| 48 h | 58.23$^{b}$ | 56.07$^{c}$ | 60.19$^{ab}$ | 58.38$^{ab}$ |
| Kinetics | | | | |
| a | 19.28 | 19.90 | 19.11 | 18.80 |
| b | 40.48 | 37.67 | 43.59 | 41.54 |
| c, h$^{-1}$ | 0.078 | 0.076 | 0.069 | 0.070 |
| Lag | 1.89$^{b}$ | 3.67$^{a}$ | 2.87$^{ab}$ | 1.91$^{b}$ |
| Potential | 59.76$^{bc}$ | 57.57$^{c}$ | 62.70$^{a}$ | 60.34$^{b}$ |
| Effective | 39.87$^{b}$ | 36.66$^{b}$ | 38.84$^{b}$ | 38.94$^{b}$ |

[1] PA = *Pichia anomala*; CE = enzymes with a chitinase activity; BPA = Propionic Acid; CON = Control.
[2] Means in the same row with different superscripts differ (P < 0.05).
[3] Parameters calculated from the fitted equation: $p = a + b[1 - e^{-c(t-lag)}]$ for $t >$ lag; where p is the proportion (%) of NDF disappearing from nylon bags after t hours of incubation; a is the rapidly disappearing fraction (%); b is the slowly disappearing fraction (%); c is the fractional rate of disappearance (h$^{-1}$) of fraction b.

Although there were no differences between the treatments in terms of the rate of NDF disappearance, the rapidly disappearing fraction and slowly disappearing fraction, effective disappearance was highest in hay treated with *P. anomala* compared to all other treatments (Table 6). The longest lag time in NDF disappearance was observed in hay treated with enzymes with a chitinase activity (3.67 h) while the shortest lag time of 1.89 h was observed in the *P. anomala* treatment. The latter lag time though was not different from that of the other treatments. Total NDF disappearance at 12, 24 and 48 h ranged from 37.28% (lowest) in enzymes with a chitinase activity treated hay to 41.06% (highest) in the *P. anomala* treatment with other treatments having intermediate values. A similar trend was observed in the 24 h disappearance. NDF disappearance after 48 h was lowest in enzymes with a chitinase activity treatments compared to all other treatments.

The in sacco DM disappearance data suggest that *P. anomala* increased the potentially digestible fraction, as well as the fractional rate and effective disappearance of the hay compared to the control. In fact, the effective disappearance values of *P. anomala* treated hay were superior to that of the control and propionic acid treatments.

Example 2

Hay, treatments and baling conditions

The hay was alfalfa hay and was harvested on Aug. 15, 2012 at Fort Macleod, Alberta, Canada. The alfalfa hay was wilted in field to moisture levels between about 24% and about 30%. Bale moisture was determined as in Example 1.

The application rate of the combination of *P. anomala* in combination with the enzyme having a chitinase activity was respectively 10$^{11}$ CFU and 1.5 g in 1 L of water per ton of hay. Accordingly, the application rate of the combination of *P. pentosaceus* in combination with the enzyme having a chitinase activity 10$^{11}$ CFU and 1.5 g in 1 L of water per ton of hay. Propionic acid product consisted of 68% (vol/vol) propionic acid, and was applied at a rate of 2.72 L/ton and considered as a positive control. The negative control was water, and was applied at a rate of 1 L per ton of hay. Five large round bales of about 800 kg were made in accordance with Example 1 for each treatment on the same day. Core samples from bales across all treatments were collected at day 0, 90 and 180 after baling to analyze their nutritional value, fermentation product and microbial changes.

Core samples collected on day 0 and 90, 180 after baling were subjected to microbiological and chemical analysis. Microbiological analysis was conducted to enumerate, isolate and characterize the microorganisms (total bacteria, yeasts and moulds) on appropriate plates through serial dilution.

TABLE 7

Microbial counts on alfalfa hay treated with various hay preservatives at baling

| TREATMENT | Days | Control | Pichia + enzymes | Pedio + enzymes | Propionic acid |
|---|---|---|---|---|---|
| Total | 0 | 5.92 | 5.28 | 6.22 | 6.34 |
| bacteria log | 90 | 7.79$^{ab}$ | 7.34$^{bc}$ | 6.69$^{c}$ | 8.49$^{a}$ |
| cfu/g DM | 180 | 8.27$^{a}$ | 6.25$^{b}$ | 6.08$^{b}$ | 8.25$^{a}$ |
| YEAST | 0 | 4.94 | 4.98 | 5.86 | 5.49 |
| | 90 | 6.57 | 4.70 | 5.05 | 6.22 |
| | 180 | 5.13 | 4.69 | 4.40 | 4.89 |
| MOLD | 0 | 4.83 | 4.79 | 4.99 | 4.66 |
| | 90 | 5.89 | 5.81 | 5.85 | 5.91 |
| | 180 | 6.49$^{a}$ | 6.92$^{a}$ | 6.69$^{a}$ | 5.36$^{b}$ |

The microbiological profile of the hay after each treatment was similar at baling for total bacteria, yeast and molds even if numerical differences were recorded. After 90 days of baling, total bacteria count was reduced by the treatment with enzymes having a chitinase activity combined with *Pediococcus pentosaceus* when compared to the control and Propionic acid treatment, whereas the treatment with enzymes having a chitinase activity combined with *Pichia anomala* tended to have a lowered bacterial count. The numerical reduction of yeast was reported for the two treatments with enzymes having a chitinase activity combined with *Pichia anomala* or *Pediococcus pentosaceus* as opposed to the control and Propionic acid treatment. The mold count was not affected by the treatments except after 180 days where the mold count was reduced by the Propionic acid treatment.

Chemical analyses was conducted to determine pH, DM, total nitrogen, ammonia nitrogen, NDF, ADF, acid detergent insoluble nitrogen (ADIN), water soluble carbohydrates, volatile fatty acids (VFA) and lactic acid (LA).

TABLE 8

Chemical composition of alfalfa hay at 0, 90 and 180 day(s) after treatment with hay preservative at baling

| TREATMENT | Days | Control | Picha + enzymes | Pedio + enzymes | Propionic acid |
|---|---|---|---|---|---|
| DM % | 0 | 68.9$^{ad}$ | 76.5$^{bc}$ | 80.4$^a$ | 66.9$^d$ |
|  | 90 | 82.6$^b$ | 85.6$^a$ | 87.3$^a$ | 79.8$^c$ |
|  | 180 | 83.7$^{bc}$ | 87.9$^a$ | 88.5$^a$ | 80.1$^c$ |
| NDF % | 0 | 39.3 | 39.6 | 38.6 | 40.1 |
|  | 90 | 55.5$^a$ | 47.7$^{cd}$ | 45.2$^d$ | 53.0$^{ab}$ |
|  | 180 | 51.3 | 54.8 | 55.3 | 54.6 |
| ADF % | 0 | 28.3 | 29.4 | 28.9 | 28.7 |
|  | 90 | 39.1$^a$ | 31.6$^{cd}$ | 30.5$^d$ | 37.1$^{ab}$ |
|  | 180 | 33.7$^c$ | 37.6$^{ab}$ | 35.4$^{bc}$ | 38.2$^a$ |
| TN % | 0 | 3.7 | 3.7 | 3.5 | 3.9 |
|  | 90 | 3.7 | 3.7 | 3.8 | 4.1 |
|  | 180 | 3.8$^b$ | 3.8$^b$ | 3.8$^b$ | 4.2$^a$ |
| ADIN % N | 0 | 7.2$^a$ | 5.0$^b$ | 5.1$^b$ | 7.3$^a$ |
|  | 90 | 17.8$^a$ | 10.6$^b$ | 8.7$^b$ | 18.8$^a$ |
|  | 180 | 12.3$^b$ | 16.9$^{ab}$ | 15.4$^b$ | 20.1$^a$ | enzymes having a chitinase activity combined with *Pichia anomala* or *Pediococcus pentosaceus* enzymes having a chitinase activity combined with *Pichia anomala* or *Pediococcus pentosaceus*, enzymes having a chitinase activity combined with *Pichia anomala* or *Pediococcus pentosaceus*

TABLE 9

Fermentation product of alfalfa hay treated with different hay preservative at baling

| TREATMENT | Days | Control | Pichia + enzymes | Pedio + enzymes | Propionic acid |
|---|---|---|---|---|---|
| pH | 0 | 6.16$^b$ | 6.23$^a$ | 6.23$^a$ | 6.07$^c$ |
|  | 90 | 7.64$^a$ | 5.92$^b$ | 5.87$^b$ | 8.29$^a$ |
|  | 180 | 7.40$^{ab}$ | 6.15$^c$ | 6.03$^c$ | 7.80$^a$ |
| LA g/kg DM | 90 | 0.32 | 0.26 | 0.17 | 0.49 |
|  | 180 | 0.26 | 0.11 | 0.10 | 0.17 |
| Succinic | 90 | 0.26 | 0.25 | 0.24 | 0.20 |
|  | 180 | 0.23 | 0.23 | 0.24 | 0.28 |
| Acetic | 90 | 0.04 | 0.31 | 0.29 | 0.42 |
|  | 180 | 0.29 | 0.29 | 0.63 | 0.71 |
| Prop | 90 | NA | NA | NA | 0.08 |
|  | 180 | NA | NA | NA | 0.04 |
| Total VFA | 90 | 0.04 | 0.31 | 0.33 | 0.50 |
|  | 180 | 0.29 | 0.29 | 0.66 | 0.76 |

Hay fermentative process was not strongly impacted by the treatments with the enzymes having a chitinase activity combined with *Pichia anomala* or *Pediococcus pentosaceus* since this forage material is not prone at fermenting either. However, the lower pH after 90 days for the treatment with enzymes having a chitinase activity combined with *Pichia anomala* or *Pediococcus pentosaceus*

Core samples were collected on day 180 and evaluated for nutritional quality using in situ and in vitro methods.

In situ experiments were conducted to assess the effect of hay preservatives on the rate and extent of digestion of hay samples collected 180 days after baling. Three cows fitted with ruminal cannulas and fed a standard feedlot backgrounding diet were used. Approximately 4 g of each composite sample from each bale (replicate) per treatment was weighed into Dacron bags and incubated in triplicate in each cow for 0, 2, 6, 12, 24, 48, 72, 96, and 120 h. Bags were retrieved after incubation and processed according to LRC SOP to determine in situ ruminal DM and NDF disappearance.

TABLE 11

In situ parameters for alfalfa hay treated with hay preservatives at baling.

| TREATMENT | Control | Pichia + enzymes | Pedio + enzymes | Propionic acid |
|---|---|---|---|---|
| a | 26.61$^{bc}$ | 30.05$^{ab}$ | 33.79$^a$ | 23.64$^c$ |
| b | 46.80$^{ab}$ | 43.08$^{bc}$ | 39.67$^c$ | 51.69$^a$ |
| c | 0.05$^c$ | 0.06$^{bc}$ | 0.07$^{ab}$ | 0.04$^c$ |
| lag | 1.80$^{bc}$ | 3.90$^{abc}$ | 4.30$^{abc}$ | 1.70$^c$ |
| a + b | 73.4 | 73.1 | 73.5 | 75.3 | a = the rapidly degradable fraction
b = the slowly degradable fraction
c = the rate at which b is degraded (/h)
lag = lag time (h)

In situ data shown in Table 11 reveal a more digestible hay material for the treatments with enzymes having a chitinase activity combined with *Pichia anomala* or *Pediococcus pentosaceus*.

In vitro experiment was also conducted to assess the effect of microbial inoculants on gas production and kinetics from 180 day hay samples. Two runs by mixed rumen fluid from three cows fitted with ruminal cannulas and fed a standard feedlot backgrounding diet were conducted. Approximately 0.5 g of each composite sample of 180d hay per treatment was weighed into vial and incubated in triplicate in each run and gas were measured for 3, 6, 9, 12, 24 and 48 h. Vials were retrieved after incubation and processed according to LRC SOP to determine in vitro ruminal DM disappearance, gas production, ammonia and VFA.

TABLE 12

In vitro digestibility of alfalfa hay treated with hay preservatives at baling

| TREATMENT | Control | Pichia + enzymes | Pedio + enzymes | Propionic acid |
|---|---|---|---|---|
| DMD g/kg | 426$^d$ | 470$^b$ | 488$^b$ | 431$^d$ |
| a | 174$^c$ | 188$^{bc}$ | 196$^{ab}$ | 177$^c$ |
| c | 6.4$^c$ | 7.7$^{bc}$ | 8.4$^b$ | 6.6$^c$ |
| lag | 0.54$^a$ | 0.08$^b$ | 0.06$^b$ | 0.48$^a$ | a = Asymptotic gas production (mL g$^{-1}$ DM)
c = Fractional gas production rate fermentation rate (mL h$^{-1}$)
lag = lag time (h)

The in vitro digestibility and fermentability of the hay at 180 day confirmed the in situ outcomes of an enhanced digestibility for both treatments with enzymes having a chitinase activity combined with *Pichia anomala* or *Pediococcus pentosaceus*.

Temperature Stability

Temperature of individual bales was monitored by continuously measuring the interior temperature throughout the storage period with three (3) Dallas Thermochron iButtons (Embedded Data Systems, Lawrenceburg, KY) inserted in the interior of each bale immediately after harvest (illustrated in pictures). The temperature was recorded at 4 hours intervals for 10 weeks.

As shown in FIG. 2, the treatments with enzymes having a chitinase activity combined with *Pichia anomala* or *Pediococcus pentosaceus* both displayed a reduced average temperature over a 60 day period post baling. The Propionic acid treatment had the highest mean temperature over time.

Figure 3:
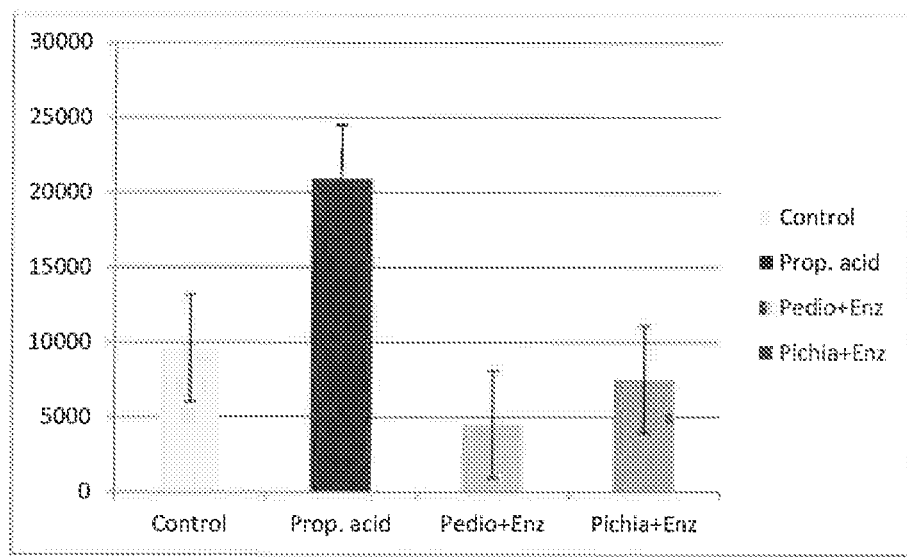
FIG. 3 illustrates a graph of the time spent in minutes above 40° C. during storage (2012) of alfalfa hay bales treated with at least one enzyme having a chitinase activity in combination with a yeast of the genus *Pichia*(Pichia+Enz) or a bacteria of the genus *Pediociccus* (Pedio+Enz), compared to alfalfa hay bales treated with Propionic acid (Prop. Acid) and non treated (Control)

The effect is particularly significant as shown in FIG. 3. FIG. 3 illustrates the time spent above 40° C. for each treatment. Since this temperature is largely recognized as the threshold for ADIN damages, it illustrates the intensity of the interior temperature of hay bales. The Propionic acid treatment spent the longest time above 40° C. The treatment with enzymes having a chitinase activity combined with *Pediococcus pentosaceus* spent the shortest time above 40° C., followed by the treatment with enzymes having a chitinase activity combined with *Pichia anomala*, both treatments with enzymes having a chitinase activity combined with *Pichia anomala* or *Pediococcus pentosaceus* spent less time above 40° C. than the control.

In conclusion, the combination of enzymes having a chitinase activity with *Pichia anomala* or *Pediococcus pentosaceus* reduced the interior temperature of hay bales, the pH and total bacteria numbers compared to the control and Propionic acid in the storage period. They also increased in situ dry matter disappearance (DMD) and rate of digestion as well as in vitro DMD and rate of gas production. This can be explained by lower NDF and ADF content in these two treatments.

Example 3

This examples shows that the enzyme having a chitinase activity is even further enhanced from the standpoint of its preservative effect and its capacity in preventing and/or reducing heat damage on high moisture hay if the at least one enzyme having a chitinase activity is combined with a yeast of the genus *Pichia* or bacteria of the genus *Pediococcus*. The hay was harvested and wilted in field to moisture levels as in example 2.

The application rate of the combination of *P. anomala* in combination with the enzyme having a chitinase activity was respectively $10^{11}$ CFU and 1.5 g in 1 L of water per ton of hay. Accordingly, the application rate of the combination of *P. pentosaceus* in combination with the enzyme having a chitinase activity $10^{11}$ CFU and 1.5 g in 1 L of water per ton of hay. The application rate of *P. anomala* alone was $10^{11}$ CFU in 1 L per ton of hay. The application rate of *P. pentosaceus* alone was $10^{11}$ CFU in 1 L per ton of hay. The enzyme having a chitinase activity alone was applied at a rate of 1.5 g (suspended in 1 L of water) per ton of hay. Propionic acid product consisted of 68% (vol/vol) propionic acid, and was applied at a rate of 2.72 L/ton and considered as a positive control. The negative control was water, and was applied at a rate of 1 L per ton of hay. Five large round bales of about 800 kg were made in accordance with Example 1 for each treatment on the same day.

As in example 2, the temperature of individual bales was monitored by continuously measuring the interior temperature throughout the storage period with three (3) Dallas Thermochron iButtons (Embedded Data Systems, Lawrenceburg, KY) inserted in the interior of each bale immediately after harvest (illustrated in pictures). The temperature was recorded at 4 hours intervals for 10 weeks. As shown in FIG. 4, when the at least one enzyme having a chitinase activity is combined with *P. anomala* or *P. pentosaceus*, the temperature reduction of high moisture hay is surprisingly significantly enhanced by the combination, in comparison with using each components of the combination.

Example 4

Objective of the Trial.

This trial expands the deployments of a proof of concept for an hay additive that would reduce heating of the bales made under challenging harvesting conditions (higher humidity content than optimal). It followed a similar trial using a laboratory scale model. The assay followed temperature profile of the small square bales (~25 kg, 79.9% DM) inoculated using different combinations of two microorganisms (*Pichia anomala* or *Pediococcus pentosaceus*) with two enzymes (pure chitinase or a commercial enzyme containing pectine lyase, glucanase and chitinase activities).

Methodology.

The trial was performed on small square bales of alfalfa-grass mix (45:55), and having a mean weight of 25.0 kg at time of harvest. The mean moisture level of the bales was of 79.9% DM, within the range of dry matter level expected (80-83% DM). The bales were inoculated with the different treatment following spraying of the forage in front of the cutting chamber of the baler, by a Dorhmann inoculant applicator. The experimental design allowed the application of a control and four different additive mixes of the microbial additives (none, *Pichia anomala*+chitinase, *Pichia anomala*+enzymes mix, *Pediococcus pentosaceus*+chitinase, *Pediococcus pentosaceus*+enzymes mix).

For each treatment, six square bales were sprayed in three blocks of two bales. The bales were transported to the storage shed, weighted and placed on pallets, in a pre-defined complete randomized pattern in a way that no surface were in contact of another bale. Each bale was fitted with a temperature probe at his geometric center. The bales were stored for 100 days.

Results.

Generally, the treatments inoculated with *Pichia anomala* (#2, and 3 in table 13) showed an effect in delaying heating of the bales, but mixing *Pichia anomala* and chitinase (#3) significantly delayed the heating and the time that temperature of the bales are 5° C. and 10° C. over ambient temperature (Table 13). This treatment also showed lower temperature during the phase between 400 and 600 hours of incubation. The addition of the enzyme mix with the *Pichia anomala* strain resulting to some numerical improvement even though the improvement was lower than with the chitinase mix.

The *Pediococcus pentosaceus* mixes (#4, and 5) allowed for a longer period before heating of the bales started. The use of both enzymes types resulted in comparable benefits with a reduction of the time spent 10° C. over the ambient temperature (Table 13).

TABLE 13

Treatment description and time related data in relation with the temperature profile

| Treatment number | Microbial additive | Enzyme additive | Time 5 Celcius above ambiant (h) | Time 10 Celcius above ambiant (h) |
|---|---|---|---|---|
| 1 | None | No | 390.6 | 290.6 a |
| 2 | Pichia anomala | Enzymes mix | 295.2 | 193.9 ab |
| 3 | Pichia anomala | Chitinase | 230.0 | 120.4 b |
| 4 | Pediococcus pentosaceus | Enzymes mix | 320.4 | 196.3 ab |
| 5 | Pediococcus pentosaceus | Chitinase | 329.6 | 224.4 ab |
| | | | P = 0.0971 | P = 0.0394 |
| | | | SEM = 58.24 | SEM = 50.43 |

While the invention has been described in connection with specific embodiments thereof, it will be understood that it is capable of further modifications and this description is intended to cover any variations, uses, or adaptations of the invention following, in general, the principles of the invention and including such departures from the present disclosure that come within known or customary practice within the art to which the invention pertains and as may be applied to the essential features hereinbefore set forth, and as follows in the scope of the appended claims.

The invention claimed is:

1. A hay preservative composition comprising an enzyme with chitinase activity and a yeast of the genus *Pichia* or a bacteria of the genus *Pediococcus*, wherein the chitinase activity is in the range of about 6 U to 250 U per ton of hay to be treated and the amount of either *Pichia* or *Pediococcus* is $10^5$ to $10^{15}$ viable organisms per ton of hay to be treated and wherein the composition is effective to reduce the heat of the hay.

2. The hay preservative composition of claim 1, wherein the *Pichia* is *Pichia anomala*.

3. The hay preservative composition of claim 2, wherein the *Pichia anomala* is *Pichia anomala* (Accession number DBVPG 3003).

4. The hay preservative composition of claim 1, wherein the *Pediococcus* is *Pediococcus pentosaceus*.

5. The hay preservative composition of claim 4, wherein the *Pediococcus pentosaceus* is *Pediococcus pentosaceus* BTC328 (Accession number NCIMB 12674) or *Pediococcus pentosaceus* BTC401 (Accession number NCIMB 12675).

6. The hay preservative composition of claim 1, further comprising at least one enzyme having a Pectin lyase activity, a Glucanase activity, or a mixture thereof.

7. The hay preservative composition of claim 1 comprising a high moisture hay.

8. The hay preservative composition of claim 7 further comprising an effective amount of *Pichia*.

9. The hay preservative composition of claim 8, wherein the *Pichia* is *Pichia anomala*.

10. The hay preservative composition of claim 9, wherein the *Pichia anomala* is *Pichia anomala* (Accession number DBVPG 3003).

11. A method of reducing heat damage in high moisture hay comprising adding the composition of claim 1 to high moisture hay.

12. The method of to claim 11, wherein the *Pichia* is *Pichia anomala*.

13. The method of claim 12, wherein the *Pichia anomala* is *Pichia anomala* (Accession number DBVPG 3003).

14. The method of claim 11, wherein the *Pediococcus* is *Pediococcus pentosaceus*.

15. The method of claim 14, wherein the *Pediococcus pentosaceus* is *Pediococcus pentosaceus* BTC328 (Accession number NCIMB 12674) or *Pediococcus pentosaceus* BTC401 (Accession number NCIMB 12675).

16. The method of claim 11, wherein the heat preserving composition further comprises at least one enzyme having a Pectin lyase activity, a Glucanase activity, or a mixture thereof.

* * * * *